(12) United States Patent
Mizutani et al.

(10) Patent No.: US 6,803,334 B2
(45) Date of Patent: Oct. 12, 2004

(54) ABSORBENT ARTICLE HAVING FIBROUS LAYER ON SURFACE

(75) Inventors: Satoshi Mizutani, Kagawa (JP); Wataru Yoshimasa, Kagawa (JP); Megumi Tokumoto, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 165 days.

(21) Appl. No.: 09/940,711

(22) Filed: Aug. 27, 2001

(65) Prior Publication Data

US 2002/0028624 A1 Mar. 7, 2002

(30) Foreign Application Priority Data

Sep. 1, 2000 (JP) ........................................ 2000-265476

(51) Int. Cl.$^7$ ................................................ B32B 27/12
(52) U.S. Cl. ...................... 442/394; 442/327; 442/352; 442/366; 428/114; 428/131; 428/141; 428/167; 428/170; 428/171; 428/198; 428/103; 428/152; 428/218; 604/358; 604/366; 604/378; 604/382; 604/385.01; 604/385.101
(58) Field of Search ................................ 442/327, 352, 442/394, 366; 428/131, 141, 198, 103, 152, 114, 167, 170, 171, 218; 604/358, 366, 378, 382, 385.01, 385.101

(56) References Cited

U.S. PATENT DOCUMENTS

| | | | | |
|---|---|---|---|---|
| 3,468,311 A | * | 9/1969 | Gallagher | .................. 604/370 |
| 4,634,440 A | | 1/1987 | Widlund et al. | ............ 604/383 |
| 4,676,786 A | * | 6/1987 | Nishino | ....................... 604/378 |
| 4,780,352 A | * | 10/1988 | Palumbo | ...................... 428/138 |
| 4,891,258 A | * | 1/1990 | Fahrenkrug | .................. 428/138 |
| 5,268,213 A | * | 12/1993 | Murakami et al. | .......... 428/163 |
| 5,990,377 A | * | 11/1999 | Chen et al. | .................. 604/381 |
| 6,362,391 B1 | * | 3/2002 | Mizutani et al. | ............ 604/379 |
| 6,646,178 B2 | * | 11/2003 | Furuya et al. | ............... 604/367 |

FOREIGN PATENT DOCUMENTS

| | | | | |
|---|---|---|---|---|
| EP | 0359502 A2 | * | 3/1990 | ........... D21H/27/00 |
| EP | 0792629 A2 | | 9/1997 | ............ A61F/13/15 |
| WO | WO 93/09741 | | 5/1993 | ............ A61F/13/15 |

OTHER PUBLICATIONS

European Search Report.

* cited by examiner

*Primary Examiner*—Elizabeth M. Cole
*Assistant Examiner*—Norca L. Torres
(74) *Attorney, Agent, or Firm*—Darby & Darby

(57) ABSTRACT

Disclosed is an absorbent article including: a liquid permeable surface layer; a backing sheet; and an absorbent layer interposed between the surface layer and the backing sheet. The surface layer includes: a porous film having a plurality of through holes; and a fibrous layer disposed on the liquid-receiving face of the porous film. The fibrous layer is of a plurality of strips extending in parallel and spaced apart from each other. Each strip of the fibrous layer is fixed to the porous film at spaced fixing portions, so that the porous film is exposed between adjacent strips of the fibrous layer.

12 Claims, 6 Drawing Sheets

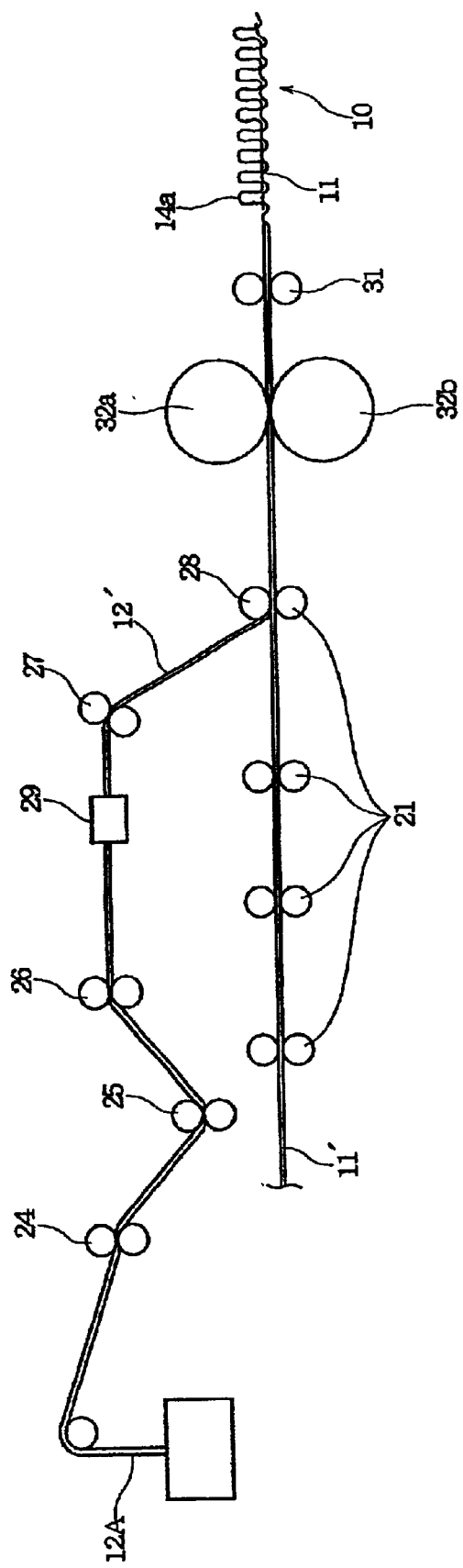

ABSORBENT ARTICLE HAVING FIBROUS LAYER ON SURFACE

BACKGROUND OF THE INVENTION

1. Field of the Invention

The present invention relates to an absorbent article having a surface layer, in which a porous film and a fibrous layer are combined, for increasing the wearer's comfort during wear.

2. Description of the Related Art

Absorbent articles, such as sanitary napkin, disposable diaper or the like are typically of construction in which an absorbent layer is laid over a liquid impermeable backing sheet, and a liquid permeable surface material is laid over the liquid receiving side of the absorbent layer.

As the surface material, it is known in the art to use a synthetic resin film sheet formed with a large number of through holes. In this film sheet, the large number of through holes function as courses or ducts for permitting passage of liquid. Therefore, the liquid applied to the sheet surface is permitted to pass through the holes to be absorbed in the absorbent layer. Hereinafter, such a film with holes is referred to as a porous film.

This porous film sheet never exhibits capillary action for retaining liquid around the through holes, unlike a non-woven fabric made of fiber aggregate. Therefore, the liquid applied to the film sheet surface can be easily guided to flow into the through holes. In addition, by adding inorganic filler into the film sheet for whitening, the film sheet can conceal the menstrual blood or the like absorbed in the absorbent layer through the through holes.

However, the porous film sheet is liable to stick to the skin of a wearer. Therefore, it hardly follows motion of the wearer's skin to thereby possibly provide irritation to the skin. In addition, the porous film sheet is inferior in the function of pulling (attracting) fine drops of liquid from the wearer's skin to the sheet, as compared with a non-woven fabric. As a result, it is liable to provide wet feeling to the wearer's skin.

On the other hand, also known are a sheet in which a resin layer is formed into strips on the surface of the porous film sheet, and a sheet in which a thin non-woven fabric is laid over the entire surface of the porous film sheet. These sheets are intended to make advantage of the merits of the porous film sheet.

However, although the former can reduce the contact area with the wearer's skin, it still remains difficult to follow motion of the wearer's skin. Therefore, it is difficult to prevent irritation to the skin. On the other hand, although the latter can provide soft contact feeling to the wearer's skin, the non-woven fabric is liable to retain liquid by capillary action of fibers forming the non-woven fabric. Therefore, it is liable to provide wet feeling to the wearer's skin.

SUMMARY OF THE INVENTION

The present invention has been worked out in view of the shortcoming in the prior art set forth above. It is therefore an object of the present invention to provide an absorbent article which makes merit of a porous film, provides soft contact feeling to the skin of a wearer, and hardly causes retention of fluid.

According to the invention, there is provided an absorbent article comprising: a liquid permeable surface layer; a backing sheet; and an absorbent layer interposed between the surface layer and the backing sheet, the surface layer including: a porous film having a plurality of through holes; and a fibrous layer disposed on the liquid-receiving face of the porous film, the fibrous layer being of a plurality of strips extending in parallel and spaced apart from each other, each strip of the fibrous layer being fixed to the porous film at spaced fixing portions, so that the porous film is exposed between adjacent strips of the fibrous layer.

The absorbent article according to the present invention can easily guide the liquid to the absorbent layer through the holes in the porous film. With the strips of the fibrous layer, moreover, the absorbent article can provides soft contact feeling to the skin of a wearer. Since fibers appearing on the surface of the fibrous layer can follow motion of the skin of a wearer, still moreover, irritation to the wearer's skin can be reduced.

Preferably, the fixing portions are spaced apart from each other in a direction along which the strips of the fibrous layer extend, and each strip is raised between adjacent fixing portions away from the porous film, to form a plurality of loop portions. In this construction, fibers on the surfaces of the loop portions can easily move in any directions to follow motion of the skin of a wearer. Moreover, the liquid can flow down along the slope of the loop portion toward the porous film so that the liquid can be easily guided to the through holes.

For example, the porous film may be contracted in the direction along which the strips of the fibrous layer extend, after the strips are fixed to the porous film, for reducing the pitch between adjacent fixing portions for raising the loop portions. In this construction, the porous film may be formed of a stretchable synthetic resin film. In an alternative, the absorbent article may further comprise an elastic member fixed on the porous film, for providing contracting force to the porous film. In another alternative, the porous film may be formed of a heat-shrinkable synthetic resin film. In the case where the porous film is formed of the stretchable synthetic resin film, it is preferred that the through holes are opened in a quadrangular shape, so that the porous film is formed with separation strips separating adjacent quadrangular through holes, the separation strips extending oblique relative to the direction along which the strips of the fibrous layer extend.

Preferably, a total length L along the outermost surface of each loop portion, between adjacent fixing portions, is in a range of 1.1 to 4 times of a pitch P between adjacent fixing portions.

For example, the fibrous layer may be formed of a bundle of continuous filaments. Alternatively, the fibrous layer may be formed of a non-woven fabric. In this case, it is preferred that each strip of the fibrous layer is formed of a bundle of thin strips formed by cutting the non-woven fabric.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings:

FIG. 10 is an explanatory illustration showing steps of one example of a manufacturing process of the absorbent article according to the present invention.

DESCRIPTION OF THE PREFERRED EMBODIMENT

The present invention will be discussed hereinafter in detail in terms of the preferred embodiment of an absorbent article according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure are not shown in detail in order to avoid unnecessary obscurity of the present invention.

Figure 1:
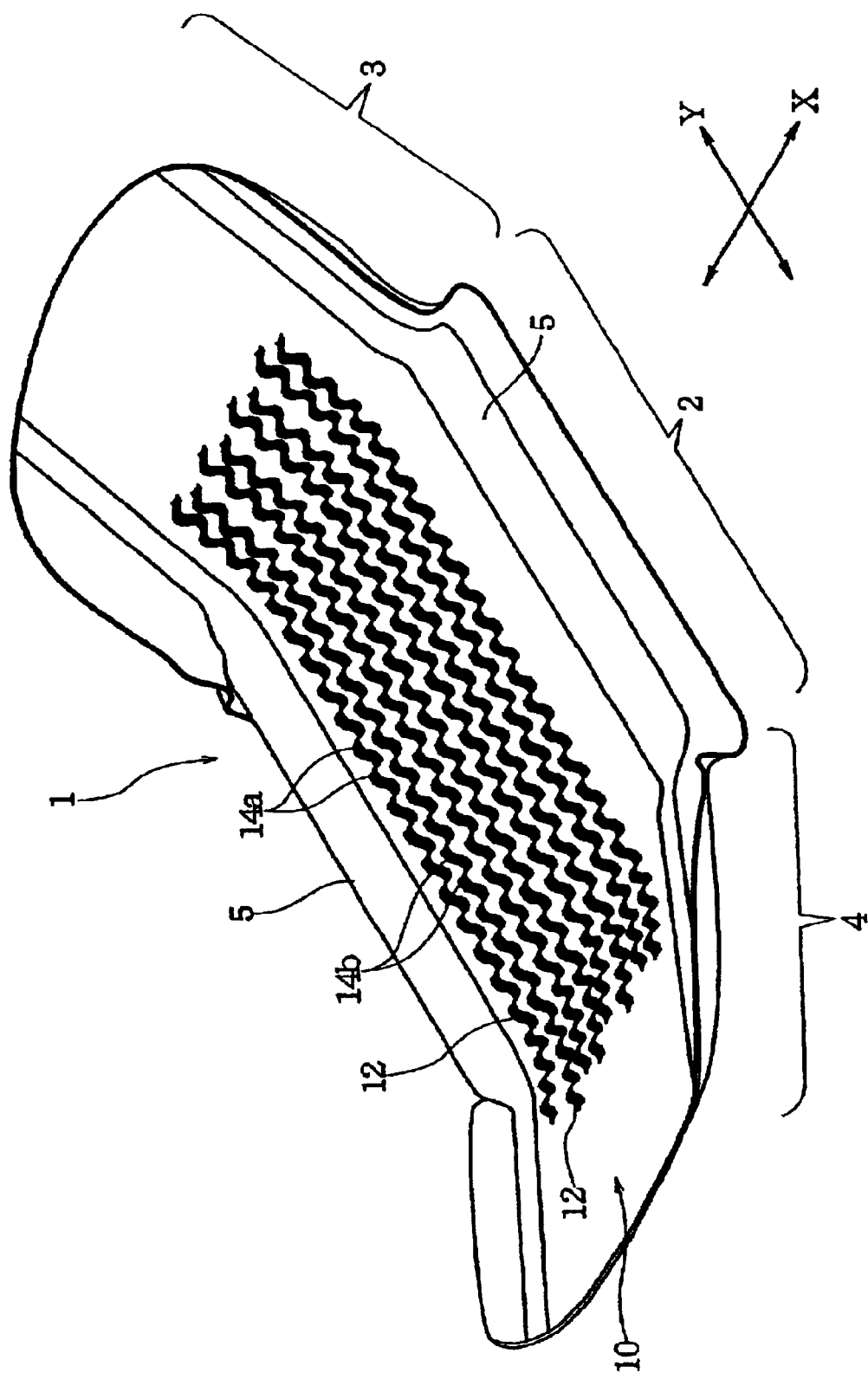
FIG. 1 is a perspective view showing an absorbent article according to a first embodiment of the present invention.
Figure 2:
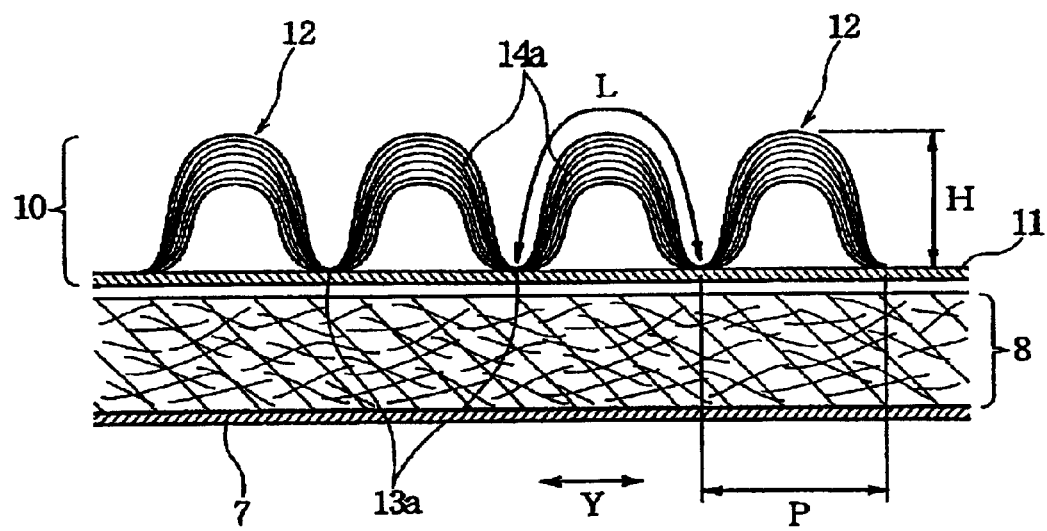
FIG. 2 is a partial section of the absorbent article shown in FIG. 1.
Figure 3:
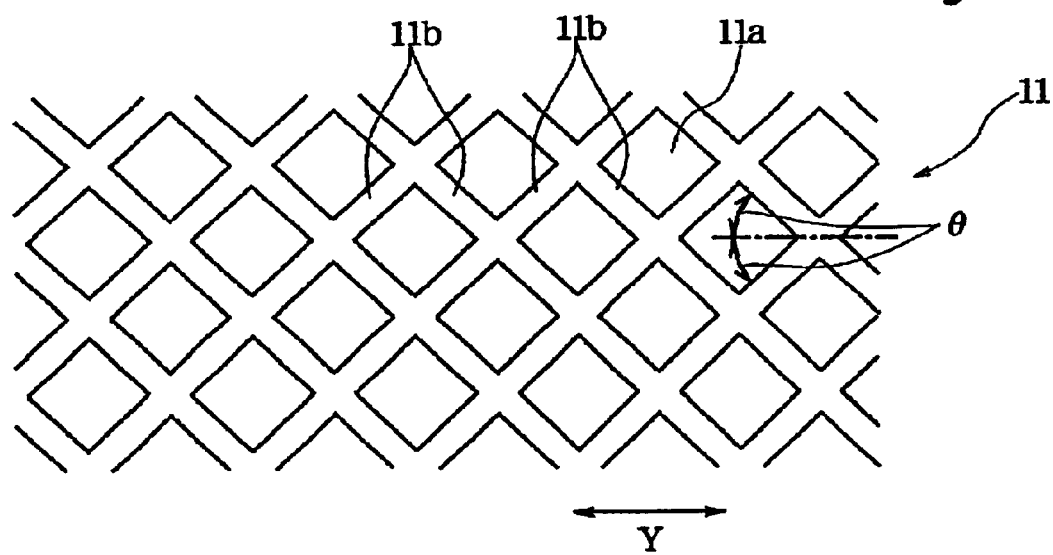
FIG. 3 is an enlarged plan view showing one example of a preferred porous film.
Figure 4:
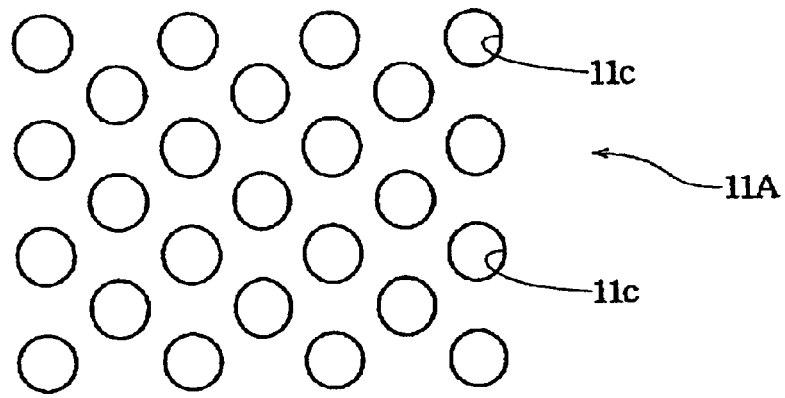
FIG. 4 is an enlarged plan view showing another example of the porous film.
Figure 6:
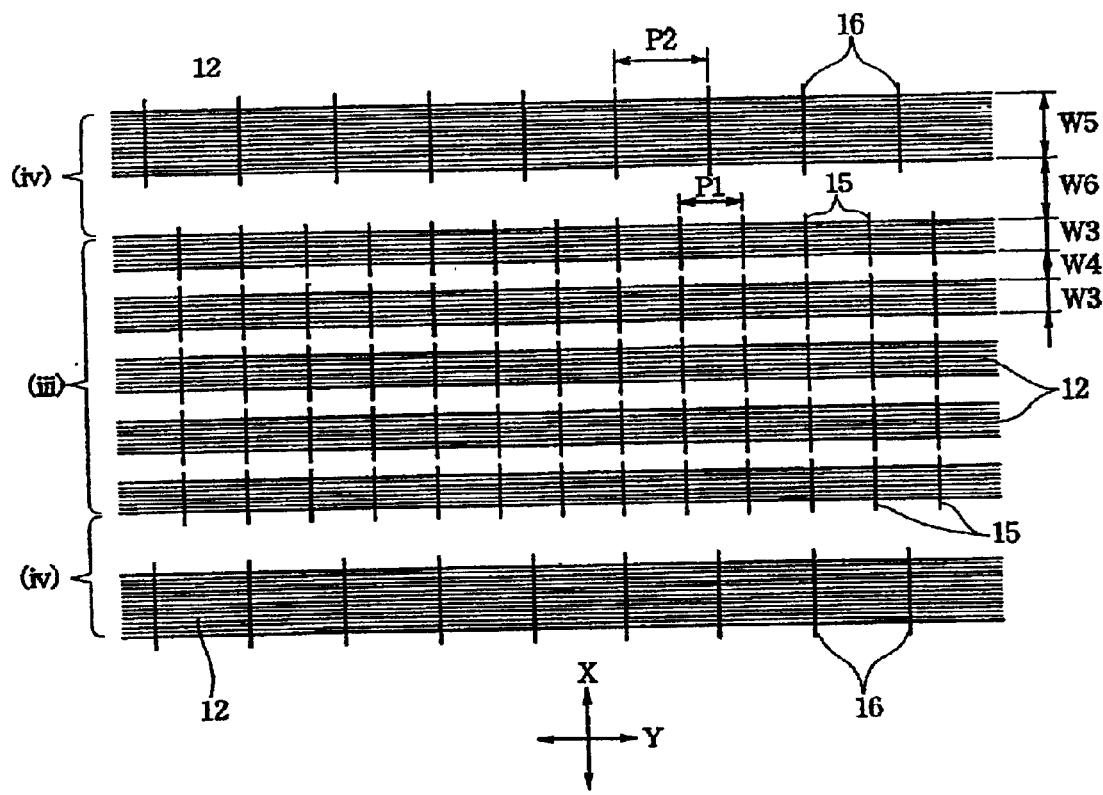
FIG. 6 is a plan view showing another example of fixing pattern of a fibrous layer and a porous film.
Figure 7:
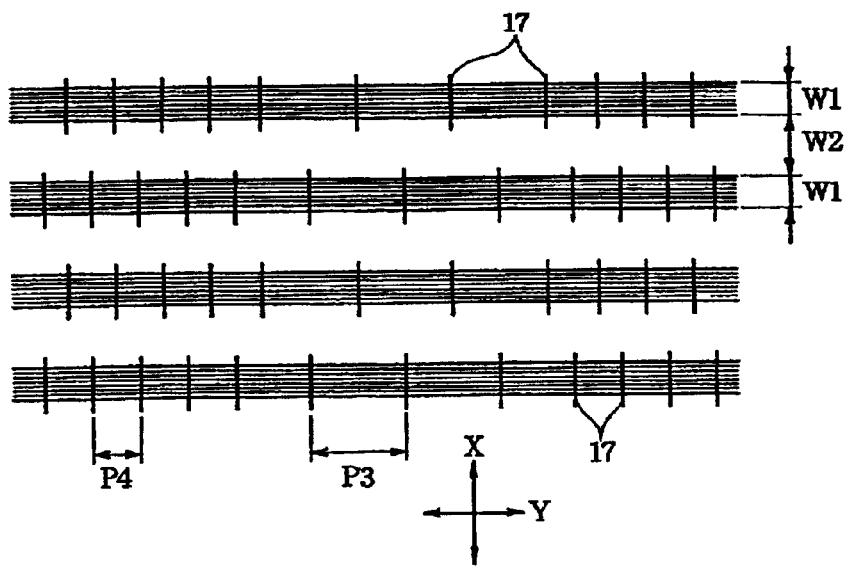
FIG. 7 is a plan view showing a further example of fixing pattern of a fibrous layer and a porous film.
Figure 8:
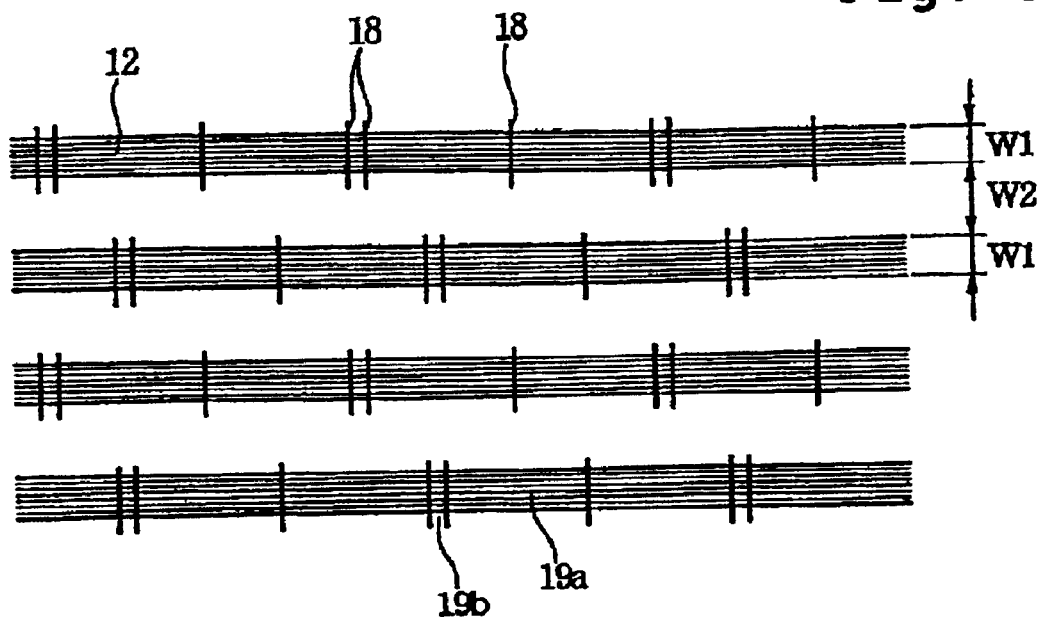
FIG. 8 is a plan view showing a still further example of fixing pattern of a fibrous layer and a porous film.
Figure 9:
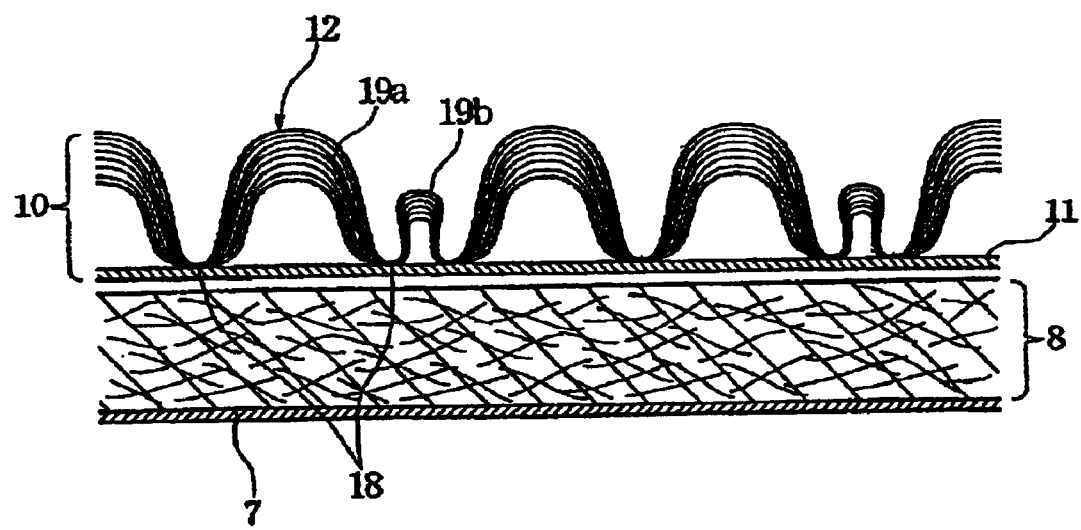
FIG. 9 is a partial section of FIG. 8.

FIG. 1 is a perspective view showing an absorbent article according to a first embodiment of the present invention, FIG. 2 is a partial section of the absorbent article shown in FIG. 1, FIGS. 3 and 4 are enlarged plan views showing examples of a preferred porous film, FIGS. 5 to 8 are partial plan views showing examples of fixing portion pattern for fixing a fibrous layer, and FIG. 9 is a partial section of FIG. 8.

An absorbent article 1 shown in FIG. 1 is a sanitary napkin. Throughout the disclosure and claims, a direction identified by an arrow X is referred to as width or lateral direction and a direction identified by an arrow Y is referred to as longitudinal direction. The absorbent article 1 has an intermediate portion 2, and a front portion 3 and a rear portion 4 located at opposite sides of the intermediate portion 2. On both side portions of a main body of the absorbent article 1, side leakage preventing walls 5 and 5 extending in longitudinal direction are provided. To the side leakage preventing walls 5 and 5, elastic members are provided for applying elastic contractive force in the longitudinal direction. By the contractive force, the main body of the absorbent article 1 is bowed in the longitudinal direction (Y direction) and the side leakage preventing walls 5 and 5 are raised up from the liquid-receiving face of the main body, mainly at the intermediate portion 2, to form three-dimensional shape.

As shown in FIG. 2, the main body of the absorbent article 1 comprises a liquid impermeable backing sheet 7, an absorbent core (absorbent layer) 8 and a liquid permeable surface layer 10, which are stacked upward in the order named above. The surface layer 10 includes a porous film 11 and a fibrous layer 12 stacked thereon. As used herein, the term "porous film" refers to a film formed with a plurality of through holes.

The absorbent core 8 is provided to extend over a part of the front portion 3, the intermediate portion 2, and a part of the rear portion 4 of absorbent article 1. In an outer peripheral region beyond the outline of the absorbent core 8, the backing sheet 7 and the porous film 11 are adhered to each other with a hot melt adhesive or fusion bonded (welded) to each other by hot embossing.

In the surface layer 10, the fibrous layer 12 is arranged in the form of spaced strips having a predetermined width and extending in parallel relationship. In the shown embodiment illustrated in FIG. 1, the fibrous layer 12 is disposed between the side leakage preventing walls 5 and 5 in the intermediate portion 2 as a primary liquid absorbing region, and also extends to parts of the front portion 3 and the rear portion 4. However, the fibrous layer 12 may be provided only in the intermediate portion 2 as the primary liquid absorbing region, especially only at the center portion thereof, if desired. In the alternative, the fibrous layer 12 may be provided to extend over the entire length of the absorbent article 1 in the Y direction, i.e., from the longitudinal end of the front portion 3, through the intermediate portion 2, to the longitudinal end of the rear portion 4.

Normally, in case of the sanitary napkin, it is preferred that the fibrous layer 12 is in a range of at least 50 to 100 mm in the longitudinal direction (Y direction) and in a range of at least 10 to 80 mm in the lateral direction (X direction).

The backing sheet 7 is liquid impermeable and is formed from a water vapor permeable resin film, a non-woven fabric or a laminate of a resin film and a non-woven fabric. The absorbent core 8 is formed by mixing crushed pulp and SAP (superabsorbent polymer), followed by wrapping the mixture in liquid permeable paper. In the alternative, the absorbent core 8 may also be formed from air laid pulp formed into a sheet by a binder process, absorbent paper, or a non-woven fabric primarily consisted of hydrophilic fibers.

The side leakage preventing wall 5 is formed from a non-woven fabric, such as through-air bonded non-woven fabric, point bonded non-woven fabric, spun bonded non-woven fabric, spun laced non-woven fabric, melt blown non-woven fabric, or air laid non-woven fabric.

The porous film 11 forming the surface layer 10 has an elastic stretchability at least in the Y direction. On the surface of the porous film 11, the fibrous layer 12 is fixed (joined). In the embodiment shown in FIGS. 1 to 5, widths W1 of the individual strips of the fibrous layer 12 in the X direction are the same relative with each other, and distances (intervals) W2 between respective of adjacent strips of the fibrous layer 12 are the same. Between the adjacent strips of the fibrous layer 12, the porous film 11 and a large number of through holes (openings) 11a or 11c formed in the porous film 11 are exposed (see FIGS. 3 and 4).

The preferred range of the width W1 is from 1.0 to 10 mm, and the preferred range of the distance W2 is from 0.5 to 10 mm. In a region where the fibrous layer 12 is provided, the area ratio of the fibrous layer 12 to the porous film 11 (i.e., the ratio of the area occupied by the fibrous layer 12 to the surface area of porous film 11) is preferably in a range of 5 to 30%.

When the area ratio of the fibrous layer 12 exceeds the foregoing range, most of the liquid applied to the surface layer 10 is retained by the fibrous layer 12, so that too much liquid resides in the surface of the surface layer 10. Therefore, the surface layer 10 is liable to provide wet feeling to a wearer. When the area ratio of the fibrous layer 12 is less than the foregoing range, the area of the porous film 11 to be exposed becomes so large as to make possibility that the surface of the porous film 11 is in contact with the wearer's skin higher, and whereby to increase possibility of providing irritation to the wearer's skin.

Figure 5:
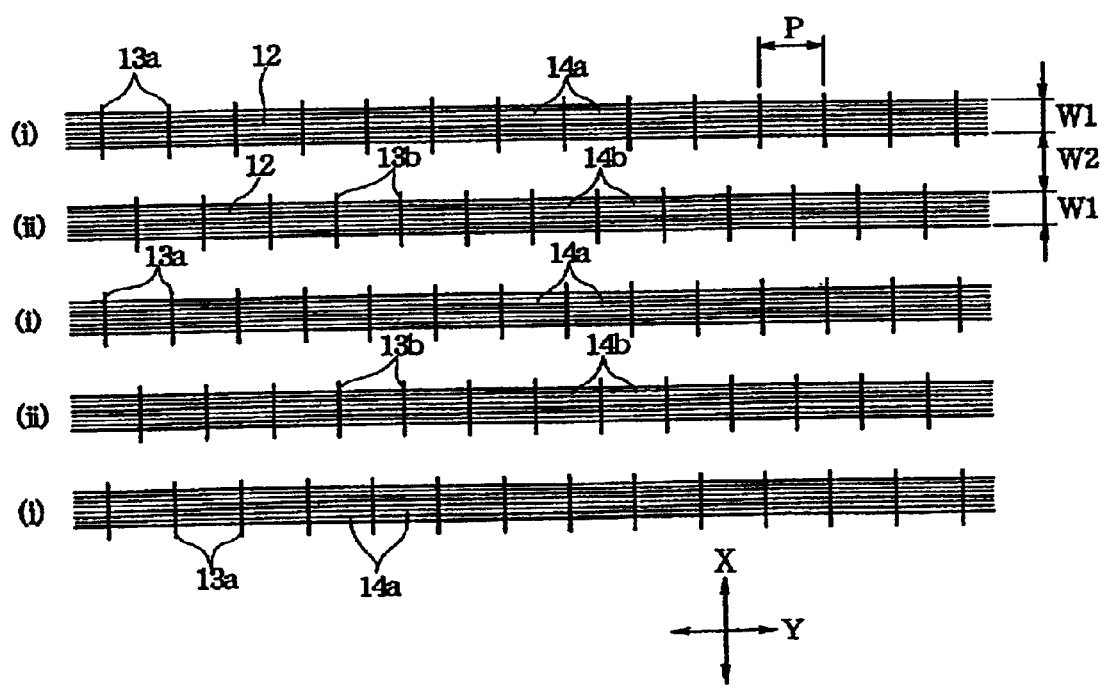
FIG. 5 is a plan view showing one example of fixing pattern of a fibrous layer and a porous film.

As shown in FIG. 5, the individual strips of the fibrous layer 12 are indicated at (i) or (ii). The strips indicated at (i) are referred to as odd number strips; and the strips indicated at (ii) are referred to as even number strips. The individual odd number strips (i) are fixed on the porous film 11 at fixing lines 13a formed at a constant pitch P in a direction along which the fibrous layer 12 extends. On the other hand, the individual even number strips (ii) are fixed on the porous film 11 at fixing lines 13b formed at a constant pitch P in the direction along which the fibrous layer 12 extends.

The individual odd number strips (i) are protruded between adjacent fixing lines 13a toward the surface side to form loop portions 14a. The individual even number strips (ii) are also protruded between adjacent fixing lines 13b toward the surface side to form loop portions 14b. The fixing lines 13a of the odd number strips (i) are offset from the fixing lines 13b of the even number strips (ii) by half the pitch P. In other words, the fixing lines 13a and 13b are arranged in such relation that one fixing line 13a is located at mid-point between adjacent fixing lines 13b and 13b. Therefore, the peaks of the loop portions 14a and the peaks of the loop portions 14b alternate with each other in the Y direction.

In the shown embodiment, the porous film 11 is elastically stretchable and the loop portions 14a and 14b are formed in the following manner. First, the strips of the fibrous layer 12 are stacked on the elastically stretchable porous film 11 in a condition where the porous film 11 is stretched and are fixed to the stretched porous film 11 at respective fixing lines 13a and 13b. Thereafter, stretching force on the porous film 11 is released to contract the porous film 11 by elastic contracting force to restore the original condition. At this time, the interval between adjacent fixing lines 13a and the interval between adjacent fixing lines 13b are reduced to form the loop portions 14a and 14b projecting from the surface of the porous film 11 by the fibrous layer 12.

In the absorbent article 1, as worn, the loop portions 14a and 14b primarily contact with the skin of a wearer. This reduces the possibility that porous film 11 will come into direct contact with the skin of a wearer. Since the strips are protruded to form the loop portions 14a and 14b, the fibrous layer 12 is flexible enough to be easily deformed in the X and Y directions. Therefore, the fibrous layer 12 may flexibly follow motion of the wearer's skin to hardly give irritating feeling to the wearer's skin. More specifically, the fibrous layer 12 is fixed only at the fixing lines 13a and 13b to form the loop portions 14a and 14b so that the individual loop portions 14a and 14b may move independently of each other as skin-contacting portions for individually following motion of the wearer's skin. Therefore, the fibrous layer 12 does not apply excessively irritating feeling on the wearer's skin.

On the other hand, as shown in FIG. 2, since the individual loop portions 14a and 14b are formed by raising the fibrous layer 12 from the surface of the porous film 11, they have high bulk restoration ability against a compression force from the above. Therefore, even if the loop portions 14a and 14b are crushed by the pressure from the skin of a wearer, they can easily recover to its original shape.

In order to form the loop portions 14a and 14b having such high bulk restoration ability as set forth above, the pitch P of the fixing lines 13a and 13b is preferably in a range of 3 to 15 mm. In addition, it is preferred that a ratio of the height H to the pitch P is in a range of 0.5 to 2, wherein the height H is measured from the surface of the porous film 11 to the peak of each loop portion 14a and 14b (See FIG. 2). Also, the height H is preferably in a range of 2 to 15 mm.

Moreover, a total length L along the outermost surface of each loop portion 14a and 14b, between adjacent fixing lines, is preferably in a range of 1 to 5 times of the pitch P, and more preferably in a range of 1.1 to 4 times thereof.

As shown in FIG. 2, since the fibrous layer 12 is raised from the surface of the porous film 11 at respective loop portions 14a and 14b, the liquid applied to the fibrous layer 12 may easily flow down toward the porous film 11 to be easily absorbed in the absorbent core 8 through the holes 11a or 11c of the porous film 11. On the other hand, since the holes of the porous film 11 are exposed between adjacent strips of the fibrous layer 12, the liquid applied to the surface layer 10 may easily flow into the holes. This can prevent the liquid from being retained in the surface layer 10.

On the other hand, since the individual strips of the fibrous layer 12 are separated by the fixing lines 13a or 13b, even if the liquid applied to the fibrous layer 12 is spread by capillary effect, the fixing lines serve to shut down propagation of spreading liquid. Therefore, the liquid can be prevented from spreading over the surface of the surface layer 10 not to give wet feeling to the wearer.

FIG. 3 is an enlarged partial plan view showing the preferred embodiment of the porous film 11. In the shown porous film 11, there are formed a large number of holes 11a of quadrangular shape (e.g. rhombus shape). Straight separation strips 11b separating adjacent quadrangular holes 11a extend in oblique relative to the longitudinal axis (Y direction axis) of the porous film. A tilting angle θ of each straight separation strip 11b with respect to the longitudinal axis is preferably in a range of 30 to 70. In the preferred embodiment, an opening area of each individual quadrangular hole 11a is in a range of 0.38 to 7.0 mm$^2$, and opening area ratio of the holes 11a is in a range of 20 to 60%.

The porous film 11 having the straight separation strips 11b can be stretched in the Y direction by smaller stretching load. When stretched, the holes 11a is elongated in the Y direction with reducing the tilting angle θ. By releasing the stretching load or force, then, the porous film 11 will be elastically contracted to restore its original shape.

The porous film 11 may be prepared by forming the holes 11a in a film formed of thermoplastic resin, such as LLDPE, LDPE, HDPE, PP, EVA or the like, or mixtures thereof, or a film formed of thermoplastic synthetic rubber, such as SEBS, SBSSIS, SEEPS, urethane or the like.

In view of formation of the loop portions 14a and 14b, when 3 to 50% of tensile strain in the Y direction is applied to the porous film 11, the restoration ratio (elastic recovery) from strain is preferably greater than or equal to 60%.

It is further preferred that the surface of the resin film is treated to be hydrophilic by applying a surface active agent on the surface of the resin film or by kneading a surface active agent in the resin film. If the porous film 11 is treated to be hydrophilic, the liquid applied on the film surface easily flows into the holes 11a. Furthermore, in order to reduce contact area to contact with the wearer's skin for lowering irritation, it is preferred to provide small unevenness on the film surface. It is also preferred to blend a whitening inorganic filler, such as titanium oxide, in the resin film forming the porous film 11.

On the other hand, it is also possible to use a porous film 11A formed with a plurality of circular holes 11c as shown in FIG. 4.

For forming the fibrous layer 12, a bundle of continuous filaments extending in the Y direction is preferably used. For example, it is preferred that a tow (i.e., a bundle of continuous filaments) is opened and widened (spread) to have a uniform thickness and is then divided (separated) into a plurality of strips having a predetermined width, for forming the individual strips of the fibrous layer 12.

In the case where the fibrous layer 12 is formed of the bundle of the continuous filaments, a fineness of the continuous filaments is preferably in a range of 1.1 to 8.8 dtex. Within this range, the loop portions 14a and 14b may restore original condition after deformation in the X direction and Y direction, and may restore original loop condition after exertion of compressing force in vertical direction. If the fineness is less than the range set forth above, the loop portions 14a and 14b should lack elastic restoration ability. On the other hand, when the fineness exceeds the range set forth above, the filaments should give stiff feeling to the wearer's skin.

Moreover, the continuous filaments as used herein are preferably crimped. In this case, individual crimped continuous filaments in respective loop portions 14a and 14b will be appropriately entangled one another while maintaining independency to some degree. Thus, in the loop portions 14a and 14b, individual filaments may have freedom in motion but are cooperative in elastic restoration. Here, the continuous filaments may be crimped by a crimper upon production of filaments, and number of crimp may further be increased for use by processing them with a pre-heating calender or with hot air. Alternatively, the continuous filaments may be crimped in coil form by causing strain in the orientation of resin forming the filaments by repeating drawing and relaxing of the filaments when they pass through a pre-heating calender.

In the crimping condition of the continuous filament, number of crimp of individual filament per 1 inch is preferably in a range of 5 to 40, and more preferably in a range of 5 to 30, and the most preferably in a range of 15 to 30. Also, crimp modulus of elasticity of the continuous filament is preferably greater than or equal to 70%.

Number of crimp is based on JIS L-1015 and crimp modulus of elasticity is based on JIS L-1074. In case of the filament of a fineness less than 5.5 dtex, an initial load of 0.49 mN is applied in pulling direction, and in case of the filament of a fineness greater than or equal to 5.5 dtex, an initial load of 0.98 mN is applied in pulling direction. Number of crimp referred to is number of threads (peaks) per 1 inch (25 mm) when the initial load is applied.

On the other hand, the crimp modulus of elasticity is expressed by:

$$\{(b-c)/(b-a)\} \times 100 (\%)$$

wherein a is a length of filament when the initial load is applied, b is a length when the crimp is stretched by applying a tension force of 4.9 mN per 1.1 dtex for 30 seconds, and c is a length as applied the initial load again after 2 minutes from releasing of the tension force.

Also, a strength of the fibrous layer 12 in the Y direction in the condition where continuous filaments are entangled by crimp is preferably greater than or equal to 0.14 N/inch. Here, the strength referred to is expressed by a load at break, when the layer of continuous filaments having a basis weight of 25 g/m$^2$ is formed in carding process, ten layers are laminated to form a test sample, the test sample is clamped to have a chuck-to-chuck distance of 100 mm by Tensilon tensile test machine, and chuck-to-chuck distance is increased at a speed (ratio) of 100 mm/min.

When the loop portions 14a and 14b are formed by such continuous filaments, soft touch to skin is achieved and each individual loop may move freely. Furthermore, such loop portions 14a and 14b may have superior elastic restoration ability.

In the absorbent article 1 employing the surface layer 10, when menstrual blood or the like is applied to the loop portion of the fibrous layer 12, it flows along the continuous filaments to reach the porous film 11 to be absorbed by the absorbent core 8 through the holes 11a or 11c of the porous film 11.

The fibrous layer 12 for use in the surface layer 10, having a property to infiltrate liquid and formed of continuous filaments, is preferred to have a basis weight of 20 to 200 g/m$^2$. If the basis weight is less than 20 g/m$^2$, number of continuous filament becomes too small to form a thick filament loop portion on the surface of the absorbent article 1. On the other hand, in case of the article, in which the fibrous layer 12 is fixed on the porous film 11 by heat fusion, if the basis weight of the fibrous layer 12 is less than the foregoing range, sufficient fixing strength cannot be obtained. On the other hand, if the basis weight is in excess of the foregoing range, capillary effect between the continuous filaments becomes excessively strong to cause retention of the liquid in the fibrous layer 12 to provide wet feeling to the wearer.

The continuous filaments forming the fibrous layer 12 are formed of heat-fusible hydrophobic synthetic resin so that they can be fusion bonded to the porous film 11. Examples of the continuous filaments include: mono-fibers such as those of PE (polyethylene), PP (polypropylene) or PET (polyethylene terephthalate); conjugated synthetic fibers of core-sheath structure, such as those of PE/PET or PE/PP; and conjugated fibers of side-by-side structure, such as those of PE/PET or PE/PP. The continuous filaments formed of synthetic resin are preferably treated to be hydrophilic with a hydrophilic agent being applied to their surfaces or kneaded in the resin. It is also preferred that the continuous filaments contain inorganic filler for whitening, such as titanium oxide or the like, in the content of 0.5 to 10% by weight. By whitening process, the continuous filaments may easily conceal (hide) menstrual blood absorbed in the absorbent core 8 from external view. The individual continuous filaments may have a circular or modified cross-section.

Here, it is further possible to laminate hydrophilic fibers such as those of rayon on the fibrous layer 12 in a content of 5 to 30% by weight, or to bond mono-fibers such as natural cellulose fibers to the fibrous layer 12 with an adhesive.

In an alternative, the strips of the fibrous layer 12 may be formed from flat yarns, split yarns or the like. Flat yarns are prepared by slitting (cutting) a resin film into thin strips (filaments) and by drawing the thin strips in the longitudinal direction. Here, the drawing may be omitted. Split yarns are prepared by splitting a film in a width direction to form filaments joined in net form.

In another alternative, as the fibrous layer 12, a non-woven fabric may also be employed. Examples of the non-woven fabric include a through-air bonded non-woven fabric, a point bonded non-woven fabric, a spun laced non-woven fabric, a meltblown non-woven fabric, and a composite non-woven fabric (i.e., multi-layer non-woven fabric) in which spun bonded non-woven fabric (S) and meltblown non-woven fabric (M) are laminated in SMS, SM, SSMS, SS, or the like. Amongst, a through-air bonded non-woven fabric is preferred for high air gap ratio. The non-woven fabric may be cut into a plurality of strips having a predetermined width corresponding to the width of the strips of the fibrous layer 12. Alternatively, it is also possible to slit (cut) the non-woven fabric into thin strips (filaments) having a much smaller width than the width of the strips of the fibrous layer 12, so as to form each strip of the fibrous layer 12 by bundling the thin strips of the non-woven fabric. These thin strips may be drawn in the longitudinal direction.

Preferred fibers for use in the non-woven fabric as set forth above are conjugated synthetic fibers of core-sheath structure, having sheath portion of lower melting point of resin than the core portion, such as those of PE/PP, PE/PET or PP/PP. The conjugated synthetic fibers are preferred to have a fineness of 1.6 to 6.6 dtex and a fiber length of 38 to 61 mm. These fibers are treated to be hydrophilic for use by applying a surface active agent on their surfaces or by kneading a surface active agent thereinto. It is also preferred that the fibers contain inorganic filler for whitening, such as titanium oxide or the like. With the whitening inorganic filler being contained in the fibers, the resulting non-woven fabric may provide a cloth-like appearance and may enhance the effect of concealing menstrual blood absorbed in the absorbent core 8.

The conjugated fibers may be otherwise of a hollow or modified cross-section. In an alternative, mono-fibers of a hollow or modified cross-section may be used for the non-woven fabric. In another alternative, for the non-woven fabric, there may be used fibers made of two resin components to have the hollow or modified cross-section, which are made porous by hydrolyzing them for elusion, followed by drying. The hollow fibers, modified cross-section fibers and porous fibers can easily absorb fine drops of liquid on the wearer's skin.

In still another alternative, the non-woven fabric may be formed of a mixture of hydrophobic synthetic fibers and hydrophilic fibers (such as viscose rayon, acetate rayon, natural cellulose fibers, or the like) for enhancing hydrophilic property. In this case, for example, the content of the hydrophobic synthetic fibers is in a range of 70 to 98% by weight, and the content of the hydrophilic fibers is in a range of 30 to 2% by weight.

When the non-woven fabric is used as the fibrous layer 12, the non-woven fabric is preferred to have a basis weight of 15 to 40 g/m² and an apparent bulkiness of 0.2 to 1.0 mm. Also, the non-woven fabric is preferred to have a breaking strength in the Y direction of 7.8 to 24.6 N/inch and a maximum elongation of 20 to 60%.

At the fixing lines 13a and 13b, in the shown embodiment, the porous film 11 and the fibrous layer 12 are fusion bonded by heat seal, sonic seal or the like. In the alternative, the porous film 11 and the fibrous layer 12 may be bonded with an adhesive at respective fixing lines. In the further alternative, the porous film 11 and the fibrous layer 12 may be fixed by using fusion bonding and adhesive bonding together. For the adhesive, use can be made of a pressure-sensitive adhesive. In such case, application amount of the pressure sensitive adhesive is preferably in a range of 0.5 to 5 g/m². Preferred line width (thickness) of the fixing lines 13a and 13b is preferably in a range of 0.5 to 5 mm and more preferably in a range of 0.3 to 3 mm.

In the embodiment shown in FIGS. 1 and 5, the width W1 of the individual strips of the fibrous layer 12 is constant and the distance (interval) W2 between adjacent strips of the fibrous layer 12 is also constant. However, if desired, it is possible to vary the width and the distance of the strips of the fibrous layer 12. As shown in FIG. 6, for example, the width W5 and the distance W6 may be set larger than the width W3 and the distance W4, respectively. More specifically, in the embodiment shown in FIG. 6, the strips having the width W3 are spaced apart from each other by the distance W 4 in a center region (iii); and the strips having the width W5 are spaced apart from adjacent strips having the width W3 by the distance W6 in both lateral side regions (iv) outside of the center region (iii). Furthermore, if desired, it is also possible to vary the pitch of the fixing lines. In the embodiment shown in FIG. 6, fixing lines 15 in the center region (iii) are arranged at pitch P1, and fixing lines 16 in the lateral side regions (iv) are arranged at pitch P2, wherein the pitch P1 is smaller than the pitch P2. Thus, in the embodiment shown in FIG. 6, loop portions formed between adjacent fixing lines 15 in the center region (iii) are lower than loop portions formed between adjacent fixing lines 16 in both the lateral side regions (iv).

Conversely to FIG. 6, it is also possible to set the width of individual strips, the distance between adjacent strips, and the pitch of fixing lines larger in the center region (iii) than in both the lateral side regions (iv).

In the embodiment shown in FIG. 7, the width W1 and the distance W2 in the fibrous layer 12 are constant. However, fixing lines 17 are arranged at a pitch P3 in a center region and at a pitch P4 in both longitudinal side regions outside of the center region, wherein the pitch P3 is larger than the pitch P4. Thus, loop portions formed in the center region are higher than loop portions formed in both the longitudinal side regions. In the embodiment shown in FIG. 7, since the higher loop portions are formed in the center portion of the liquid absorbing region, the absorbent article can provide soft contact feeling in this portion. Moreover, the higher loop portions can easily follow motion of the skin.

In the embodiment shown in FIG. 8, the width W1 and the distance W2 in the fibrous layer 12 are constant. On the other hand, the pitch of fixing lines 18 is varied at various positions. Therefore, as shown in FIG. 9, higher loop portions 19a are formed between adjacent fixing lines 18 arranged at a larger pitch; and lower loop portions 19b are formed between adjacent fixing lines 18 arranged at a smaller pitch. With the higher loop portions 19a, the fibers easily follow movement of the skin to reduce or eliminate irritative feeling, and with the lower loop portions 19b, liquid can be easily guided to the holes 11a or 11c.

FIG. 10 shows one example of manufacturing process of the absorbent article 1 according to the first embodiment of the present invention.

In the transporting roller group 21 transporting a continuous porous film 11', rotation speeds of respective rollers are gradually increased toward the downstream side. Therefore, the tensile force applied to the porous film 11' is increased as the film is transported by the transporting roller group 21, and as a result, the porous film 11' is stretched to have a tensile strain in a range of 5 to 50%.

On the other hand, a bundle 12A of continuous filaments called as tow, is transported by transporting rollers 24, 25 and 26. Rotation speed of the transporting roller 25 is higher than that of the transporting roller 24, and rotation speed of the transporting roller 26 is lower than that of the transporting roller 25. Accordingly, the bundle 12A is stretched between the transporting rollers 24 and 25, and is contracted between the transporting rollers 25 and 26. Stretching stage and contracting stage are repeated for a plurality of times as required, to thereby open the bundle 12A.

By spreading and separating means 29, thereafter, the opened bundle 12A is spread (widened) in the width direction to have a uniform bulkiness (thickness) and separated (divided) into a plurality of continuous strips having the width W1 and the distance W2, to thereby form a continuous fibrous layer 12'. This continuous fibrous layer 12' is then stacked on the continuous porous film 11' through the transporting rollers 27 and 28.

A transporting roller 31 is provided on downstream side of the transporting roller group 21. Rotation speed of the rightmost end roller of the transporting roller group 21 and rotation speed of the transporting roller 31 are the same so as to maintain the porous film 11' in the stretched condition. Between the transporting roller group 21 and the transporting roller 31, the fibrous layer 12' and the porous film 11' are clamped by welding rolls 32a and 32b. On one of the welding rolls 32a and 32b, emboss of the fixing line pattern as shown in FIG. 5 or the like is formed. As transported across the welding rolls 32a and 32b, therefore, the fibrous layer 12' is fixed to the porous film 11' at the fixing lines 13a and 13b. At this time, the fixing method is heat seal or sonic seal.

At downstream side of the transporting roller 31, stretching force on the porous film 11' is released. Then, by elastic contracting force of the porous film 11', the porous film 11' is uniformly contracted in the Y direction to shorten the distance between the fixing lines 13a and the distance between the fixing lines 13b to form the loop portions 14a and 14b by the fibrous layer 12'. This resulting laminate is cut into a desired size to form the surface layer 10 having the porous film 11 and the fibrous layer 12.

In addition to the process illustrated in FIG. 10, there is provided a step of disposing the absorbent core 8 on the backing sheet 7. The surface layer 10 formed with the loop portions 14a and 14b is supplied on the absorbent core 8 and is bonded by a hot melt adhesive or the like. Thus, the absorbent article 1 shown in FIG. 1 is completed.

The contraction of the porous film 11 to form the loop portions can also be caused by other means. For example, a plurality of elastic members (e.g., elastic yarns or elastic strips) extending in parallel with each other may be fixed, while being preliminarily stretched in the Y direction, to the porous film 11. Then, after the fibrous layer 12 is fixed on the porous film 11, the stretching force applied to the elastic members is released to contract the porous film 11. In this case, the porous film 11 may be or may not be elastically stretchable.

Detail of such construction employing the elastic member, such as elastic yarn, elastic strip or the like has been disclosed in commonly owned co-pending Patent Application for "ABSORBENT ARTICLE EMPLOYING SURFACE LAYER WITH CONTINUOUS FILAMENT AND MANUFACTURING PROCESS THEREOF" (with claiming convention priority based on Japanese Patent Application No. 2000-265467. Disclosure of the above-identified commonly owned co-pending application is herein incorporated by reference.

Alternatively, it is also possible to use a heat-shrinkable synthetic resin film as the porous film 11. When a heat-shrinkable porous film 11 is used, the fibrous layer 12 is stacked on the porous film 11 under room temperature environment and fixed at respective fixing lines 13a and 13b. Subsequently, the porous film 11 is heated to cause heat-shrinkage to form the loop portions 14a and 14b. As the heat-shrinkable porous film 11, a porous film provided anisotropic drawing, may be used.

If the porous film is contracted by elastic members or by heat-shrinkage, as set forth above, the holes can be tilted toward the absorbent core to enhance the effect of concealing the menstrual blood or the like absorbed in the absorbent core.

As a result of the various structures described in detail above, advantages of the invention may include one or more of the following:

(1) Since the porous film is exposed between adjacent strips of the fibrous layer, liquid applied to the surface layer, such as menstrual blood, can be quickly transferred to the absorbent layer through the holes in the porous film;

(2) Since the strips of fibrous layer preferentially come into contact with the skin of a wearer to follow motion of the wearer's skin, irritative impact on the wearer's skin can be successfully reduced;

(3) Since each strip of the fibrous layer is separated by the spaced fixing portions, the liquid applied to the fibrous layer is prevented from spreading along the strip, so that the surface layer provides less wet feeling to the wearer's skin;

(4) If there are formed the loop portions which can be easily deformed to follow motion of the wearer's skin, the irritation on the skin can be further reduced and the liquid can be easily guided to the holes in the porous film; and (5) If each strip of the fibrous layer is formed of continuous filaments or thin strips (filaments) made by cutting a non-woven fabric or film, the liquid can be easily and smoothly guided to the porous film while preventing retention of liquid by the fibrous layer and provision of wet feeling to the wearer's skin.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. An absorbent article comprising:
    a liquid permeable surface layer;
    a backing sheet; and
    an absorbent layer interposed between said surface layer and said backing sheet,
    said surface layer including: a porous film having a plurality of through holes; and a layer disposed on the liquid-receiving face of said porous film, said layer being of a plurality of fibrous layers extending longitudinally in parallel and being separated from each other at predetermined latitudinally spaced intervals, each fibrous layer being fixed to said porous film at spaced fixing portions, so that said porous film is exposed between adjacent rows of said layer.

2. The absorbent article as set forth in claim 1, wherein said fixing portions are spaced apart from each other in a longitudinal direction along which said layer extends, and between adjacent fixing portions each fibrous layer is raised away from the porous film to form a plurality of looped portions.

3. The absorbent article as set forth in claim 1, wherein said porous film is contracted in the longitudinal direction along which said layer extends, after said fibrous layers are fixed to said porous film, for reducing a pitch between adjacent fixing portions for raising looped portions.

4. The absorbent article as set forth in claim 3, wherein said porous film is formed of a stretchable synthetic resin film.

5. The absorbent article as set forth in claim 3, which further comprises an elastic member fixed on said porous film, for providing contracting force to said porous film.

6. The absorbent article as set forth in claim 3, wherein said porous film is formed of a heat-shrinkable synthetic resin film.

7. The absorbent article as set forth in claim 4, wherein said through holes are opened in a quadrangular shape, so that said porous film is formed with separation strips separating adjacent quadrangular through holes, said preparation strips extending oblique relative to the direction along which said fibrous layers of said layer extend.

8. The absorbent article as set forth in claim 2, wherein a total length L along the outermost surface of each loop portion, between adjacent fixing portions, is in a range of 1.1 to 4 times of a pitch P between adjacent fixing portions.

9. The absorbent article as set forth in claim 1, wherein said layer is formed of a bundle of continuous filaments.

10. The absorbent articles as set forth in claim 1, wherein said layer is formed of a non-woven fabric.

11. The absorbent article as set forth in claim 10, wherein each fibrous layer of said layer is formed of a bundle of thin strips formed by cutting said non-woven fabric.

12. The absorbent article as set forth in claim 1, wherein each fibrous layer is a bundle of continuous filaments opened from a tow or a bundle of thin strips cut out from a non-woven fabric.

* * * * *